US008382284B2

(12) United States Patent
Munger et al.

(10) Patent No.: US 8,382,284 B2
(45) Date of Patent: Feb. 26, 2013

(54) METHOD AND APPARATUS FOR CORRELATED OPHTHALMIC MEASUREMENTS

(75) Inventors: Rejean J. Munger, Ottawa (CA); Michael Davies, Ottawa (CA); Gordon Freedman, Nepean (CA)

(73) Assignee: Freedom 25 Investments Inc., Ottawa, Ontario (CA)

( * ) Notice: Subject to any disclaimer, the term of this patent is extended or adjusted under 35 U.S.C. 154(b) by 92 days.

(21) Appl. No.: 13/011,001

(22) Filed: Jan. 21, 2011

(65) Prior Publication Data

US 2011/0109881 A1  May 12, 2011

Related U.S. Application Data

(63) Continuation of application No. 12/007,503, filed on Jan. 11, 2008, now abandoned.

(51) Int. Cl.
*A61B 3/10* (2006.01)
*A61B 3/14* (2006.01)

(52) U.S. Cl. ........................................ 351/208; 351/205

(58) Field of Classification Search .................. 351/205, 351/208

See application file for complete search history.

(56) References Cited

U.S. PATENT DOCUMENTS

2006/0215113 A1* 9/2006 Chernyak ...................... 351/246

* cited by examiner

*Primary Examiner* — Ricky Mack
*Assistant Examiner* — Mahidere Sahle
(74) *Attorney, Agent, or Firm* — Freedman & Associates

(57) ABSTRACT

A method and system for providing multiple ophthalmic and retinal blood measurements is outlined. By extracting multiple digitized wavelength images and quantitative data within a relatively short time period the method allows for compensation of a patient's eye or head movement, generation of ophthalmic clinical records, and determination of data relating to blood measurements, such as oxygen saturation and hemoglobin, in addition to ocular and other disease determinations. The method provides for multiple analysis and measurements within a single sitting of the patient, with a single simple instrument and without adaptations to the instrument during a patient's eye examination. Beneficially the approach allows for low cost, compact, and even portable implementations offering such analysis and determination outside the current ophthalmic centers providing eased access and earlier diagnosis opportunities.

28 Claims, 3 Drawing Sheets

METHOD AND APPARATUS FOR CORRELATED OPHTHALMIC MEASUREMENTS

This application is a continuation of U.S. patent application Ser. No. 12/007,503 filed on Jan. 11, 2008, and claims the benefit of U.S. Provisional Application No. 60/879,793, filed on Jan. 11, 2007, the entire content of which is incorporated herein by reference.

FIELD OF THE INVENTION

The invention relates to ophthalmic analysis and more particularly to using time and wavelength based imaging to provide multiple analyses with reduced constraints on equipment and patient.

BACKGROUND OF THE INVENTION

Historically, visits to an eye care center or ophthalmic clinic were based upon obtaining a measure of the patient's reading quality as a function of distance, color and text dimension. Then based upon these the patient was assessed using a wide variety of graduated lenses to provide a simple three value characterization for each eye of the appropriate lens to correct for common visual defects such as shortsightedness, long-sightedness, and astigmatism.

Today such visitations to an eye care center or ophthalmic clinic include the addition of a limited but ever increasing number of testing methodologies for the detection of eye health problems (for example: glaucoma, age related macular degeneration, macular edema, diabetic retinopathy, etc) and systemic health problems such as diabetes. Generally, each such test is performed by provisioning of a further evaluation station within the center such that the patient is moved along by staff to each evaluation station in turn. At each station the patient is required to hold their head in a steady position within a restraint, and to keep their eye open for extended periods whilst the specific evaluation is performed.

Such a requirement for multiple evaluation stations places constraints on the provisioning of such ophthalmic tests for patients to locations with significant floor area, requires the centers providing the services to invest heavily in capital equipment, and provides a psychological barrier to patients in having frequent check-ups and assessments. Furthermore, a single file must pass from system to system for storing of results therein or data of one patient ends up in another patient's file. Management of patient data is important if screening tests are to be meaningful. More importantly, each testing station provides medical information unique to its testing environment (instrument design, patient positioning, imaging field, etc.) which poses a significant barrier to integrating/correlating these multiple results (such as for example identifying identical locations in the eye from each test) for making clinical decisions. Finally, the unavoidable significant time delay between the acquisition of results from each station means that there could be some changes in the patient's status (for example: patient gets tired, walking has increased heart rate, nervousness increases blood pressure, etc.) which could affect the ability of the clinician to integrate the information provided by the tests to provide a clinical assessment.

One approach to managing patient data is to test a single patient at a time. In such a situation, all systems are unused except one. This is an inefficient use of resources. Unfortunately, for a very efficient use of resources, file management becomes extremely difficult with several tests performed on different patients in parallel.

It would therefore be beneficial to provide an ophthalmic instrument that allowed a plurality of ophthalmic tests to be performed upon a patient in a single sitting with a single sequence of measurements that did not require reconfiguration of the ophthalmic instrument during the sitting. Advantageously, such a single sequence of measurements provides for quick and efficient correlation of results from these different measurements and allows for the incorporation of weightings or adjustments into the analysis of one characteristic based upon measurements and analysis of another characteristic. This being feasible as these measurements are now associated with defined time differences, the time between measurements being reduced with such a single setting and single sequence of ophthalmic measurements, and the conditions of the measurements being more consistent than moving a patient between multiple test stations over an extended period of time.

Advantageously, if the correlation between measurements is of increased interest (for example when testing for a specific condition) then the sequence of tests within the ophthalmic instrument can be changed simply, such as with software reconfiguration of the testing sequence. Further, the ability to provide consistent time differences and testing conditions between different measurements allows improved correlation of the measurements not only within a single sitting but across the multiple sittings of a patient over time with their repeat visits in order to follow changes over time. Additionally, the defined time stamps of the different measurements allows the subsequent analysis of the measurement data for an additional or new characteristic at a later date, a potential which today does not exist.

Additionally, automating multiple measurements within a single sitting provides opportunities to opportunities to expand the provisioning of the tests based upon ophthalmic measurements, including but not limited to, blood flow, oxygen saturation, etc. and allowing these tests to be deployed outside ophthalmic centers into doctor's offices, dental offices, and even wider providing opportunities for enhanced diagnosis, early identification of diseases or conditions, reduced health care expenditures, and potentially saving lives.

It is therefore an object of this invention to provide such a beneficial method of providing within a single sitting multiple ophthalmic measurements providing enhanced correlation of the measurements and analysis.

SUMMARY OF THE INVENTION

In accordance with the invention there is provided a system for performing ophthalmic measurements comprising an optical source, the optical source comprising at least a control port, the optical source for providing a source optical signal at least one of a plurality of predetermined wavelengths, the one of the plurality of predetermined wavelengths being established in dependence of a control wavelength signal provided to the control port. Also provided is a detector, the detector comprising at least an output port, the detector for receiving a detected optical signal, generating at least a digital representation of a detected optical signal, and providing the digital representation of a detected optical signal at the output port as a detected electrical signal. An optical coupling is provided for coupling the source optical signal to a patient's eyeball, receiving at least a reflected signal to an eyeball of the patient, and providing the reflected optical signal to the detector, the reflected optical signal therefore forming at least a portion of the detected optical signal.

Also provided is a controller, the controller being electrically connected to at least the control port and output port, the controller for providing at least one of a plurality of control wavelength signals, receiving the detected electrical signal, and providing a processed electrical signal, the processed electrical signal being determined at least in dependence upon the detected electrical signal, the control wavelength signal, and a predetermined factor.

In accordance with another aspect of the invention there is provided a method of providing an ophthalmic instrument, comprising at least a multi-wavelength optical source, an optical wavelength filter, and a detector. The ophthalmic instrument for providing a digital output determined in dependence upon at least a state of the machine and the wavelength of the multi-wavelength optical source. There is also provided a rest, the rest for providing a predetermined relationship between a patient's head engaged with at least the rest and the ophthalmic instrument; and thereby determining with a single placement of the patient's head with respect to the ophthalmic instrument at least one of a plurality of measurements of the patient, the measurements determined in dependence upon at least one digital output

BRIEF DESCRIPTION OF THE DRAWINGS

Exemplary embodiments of the invention will now be described in conjunction with the following drawings, in which.

DETAILED DESCRIPTION OF EMBODIMENTS OF THE INVENTION

Figure 1:
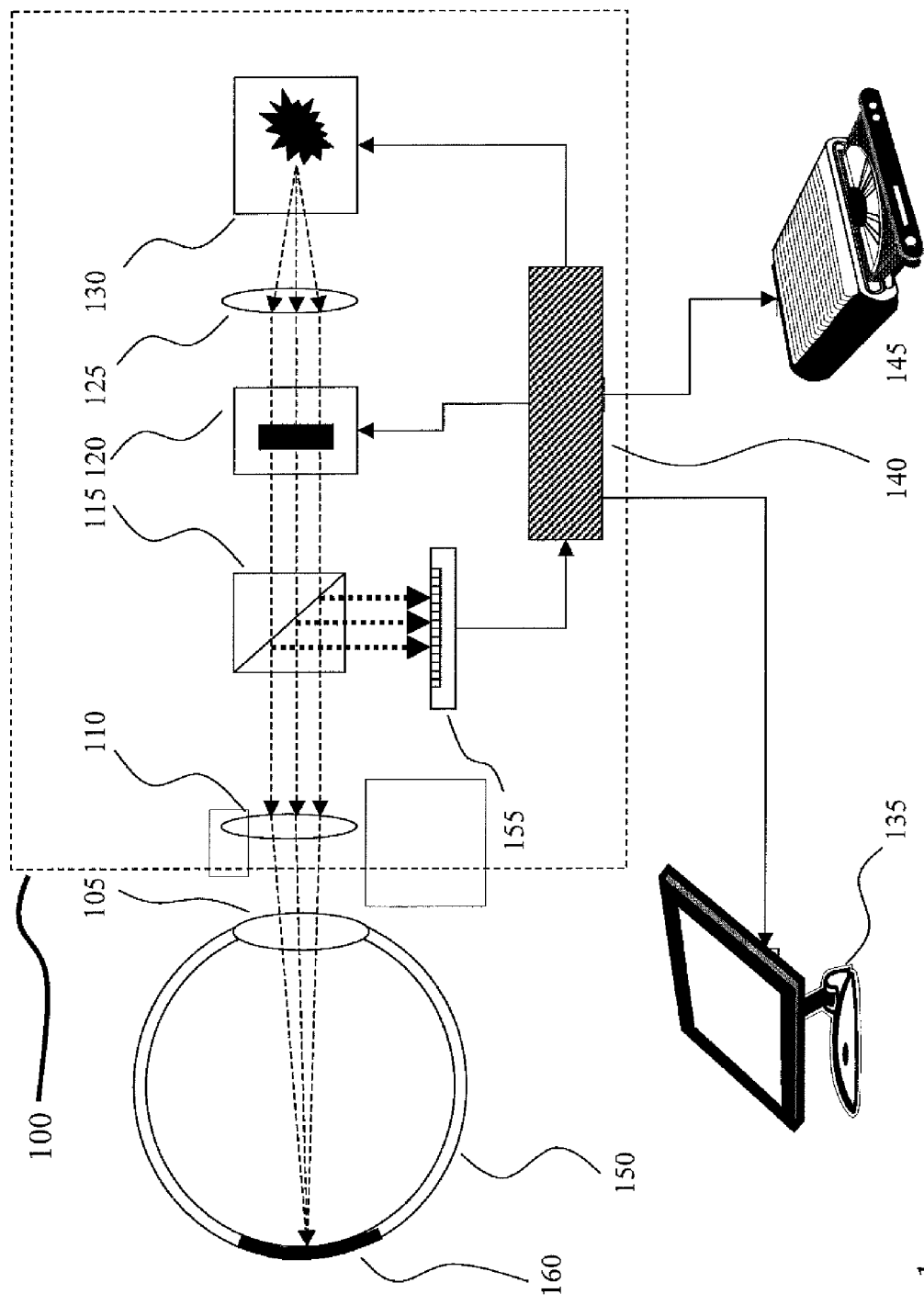
FIG. 1 illustrates a schematic of an exemplary ophthalmic system according to the invention.

Referring to FIG. 1 shown is a schematic of an exemplary ophthalmic system 100 according to the invention. Shown within the ophthalmic system 100 are an optical source 130 capable of providing light at the wavelengths necessary for the tests to be performed with the images and data extracted using the ophthalmic system 100. Such a light source typically being a tungsten lamp for high efficiency, high optical illumination and broad wavelength provisioning.

The emission from the optical source 130 is collimated using first lens 125 and coupled to a wavelength filter element 120 that selects the wavelength for a measurement to be performed. As shown the wavelength filter element 120 and optical source 125 are electrically interconnected to a central controller 140 which provides for management of the wavelength filter element 120 and optical source 125 during the measurement procedures under control of software operating upon a microprocessor, not shown for clarity but optionally embedded within the central controller 140.

The output light of the wavelength filter element 120, being a wavelength slice of the emission from the optical source 130 is coupled via optical element 115 to the second lens 110 wherein it is coupled to the patient's eyeball 150 via their corneal lens 105. Light reflected from the retina 160 of the patient's eyeball 150 is then coupled back through the corneal lens 105 and second lens 110 to the optical element 115. Optical element 115 provides the functionality of a beam splitter in that the reflected light impinging onto the optical element now exits from a port of the optical element that is not the same as the light initially coupling into the optical element 115 from the optical source 130. In this manner the reflected signal is isolated from the optical source 130. The reflected signal upon exiting the optical element 115 is coupled to a CCD array 155.

The CCD array 155 is electrically coupled to the central controller 140 allowing the image of the patient's retina 160 to be extracted. In this exemplary embodiment the extracted CCD image is provided either to a display 135 or a storage device 145. It would be evident to one skilled in the art that the CCD data may be handled in many different manners, including but not limited to being stored without processing, stored with processing, displayed with processing, processed in conjunction with an algorithm stored within the central controller, processed in conjunction with other wavelength images, have qualitative data extracted from the image, and have qualitative data extracted in dependence upon multiple extractions with varying optical source intensity. Further, the CCD image may be processed such that for all wavelengths, extracts of the images are aligned within a predetermined image template according to a physically extracted feature of an image. In this manner the ophthalmic system 100 allows for movement of the patient's eyeball 150 during a sequence of multiple images, such motion for example arising from motion of the patient's eyeball 150 itself or the patient's head, not shown for clarity.

An exemplary embodiment of the use of an ophthalmic system 100 as presented in respect of FIG. 1 is now described for an oxygen saturation measurement without calibration. The model describing the light reflection and absorption by the different layers in the human eye in this exemplary embodiment was adopted from the early model developed by van Norren & Tiemeijer (1986) and Delori & Pflibsen (1989). A similar model, which further includes the receptor layer ignored in earlier models, was presented by van de Kraats, Berendschot & van Norren (1996) and Faubert & Diaconu (2001) and may be optionally employed in this determination as could any future improvements of ocular tissue absorption models. In this model, as shown schematically in FIG. 2 the pigment epithelium 290 and the sclera 270 are the principal reflectance layers and the eye media 240, macular pigment 280, melanin 275, photoreceptor photo pigments 230, together with hemoglobin and oxygenated hemoglobin represent layers where light is absorbed.

Figure 2:
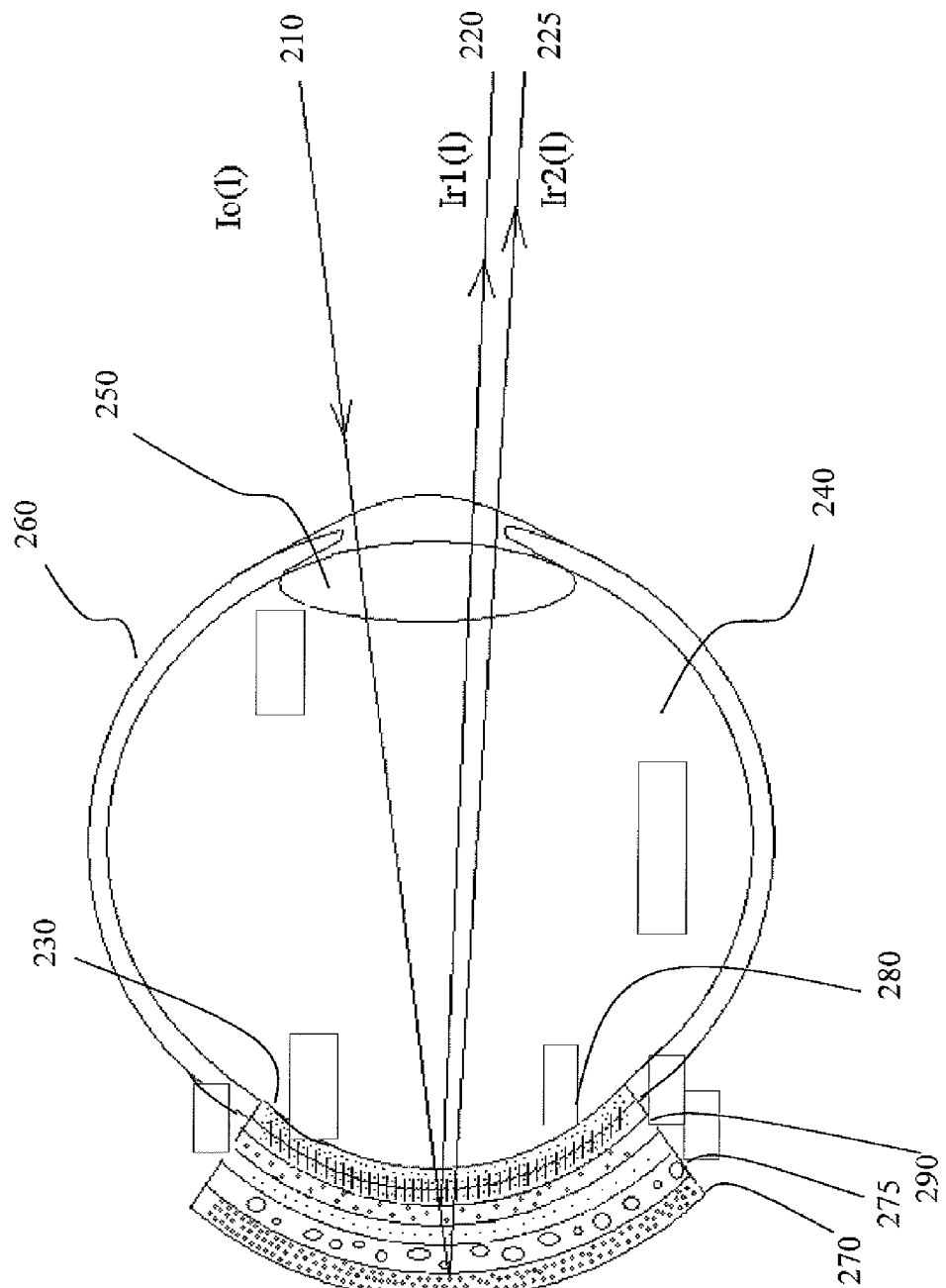
FIG. 2 illustrates an exemplary visualization of the retinal reflections as exploited by an exemplary embodiment of the invention for providing an oxygen saturation measurement without calibration.

According to FIG. 2, an incident light of intensity $I_0(\lambda)$, we obtain a reflected light with two components: one from the pigment epithelium layer 290 and one from the sclera 270. A mathematical description is shown by the following equations (1) and (2)

$$I_{R1}(\lambda) = I_0(\lambda) * 10^{-2(D1(\lambda) + D2(\lambda) + Dp(\lambda))} * R1(\lambda) * C(\lambda) \quad (1)$$

$$I_{R2}(\lambda) = I_0(\lambda) * 10^{-2(D1(\lambda) + D2(\lambda) + Dp(\lambda) + D3(\lambda) + D4(\lambda) + D5(\lambda))} * R2(\lambda) * (1 - R1(\lambda))^2 C(\Omega) \quad (2)$$

In equation (1), $I_{R1}(\lambda)$ represents the spectral flux reflected by the pigment epithelium 290 and in equation (2), $I_{R2}(\lambda)$ represents the spectral flux reflected by the sclera 270. The constant $C(\Omega)$ represents that only a small fraction of the reflected light exiting through the solid angle of the fundus point and the pupil surface. For human eye dimensions and for a typical pupil of 4 mm in diameter, $C(\lambda)$ equals approximately $10^{-2}$.

The reflection coefficients of the epithelium and the sclera are represented by the $R_1(\lambda)$ and $R_2(\lambda)$ respectively. In the equation (2) the expression $(1-R_1(\lambda))^2$ determines that the reflected light from the sclera 270 supports two partial reflections from the epithelium layer 290. The different absorbing layers are represented in the formulas by the values $Di(\lambda)$ for optical spectral density. For a homogeneous medium, the optical spectral density can be described by the following formula:

$$D(\lambda)=\epsilon(\lambda)*d*c \quad (3)$$

In equation (3), $\epsilon(\lambda)$ represents the spectral extinction coefficient, d is the optical path length of the light in the absorbing layer, and c is the concentration of the absorbing molecules in the medium. In this exemplary embodiment the optical density of different layers in the eye has been assumed to be expressed by a function $F(\lambda)$ that is constant across subjects, i.e. the normalized spectral density function is constant, multiplied by a subject dependent coefficient m:

$$D(\lambda)=F(\lambda)*m \quad (4)$$

In equation (4), m varies as a function of optical path length d and concentration c.

Hence, from Equations (1) and (2) we can express the reflected light from the fundus of the eye as:

$$I_R(\lambda)=I_{R1}(\lambda)+I_{R2}(\lambda) \quad (5a)$$

and $$I_R(\lambda)=I_0(\lambda)*10^{-2(D1(\lambda)+D2(\lambda)+Dp(\lambda))}*[R1(\lambda)+10^{-2(D3(\lambda)+D4(\lambda)+D5(\lambda))}*R2(\lambda)*(1-R1(\lambda))2]*C(\Omega) \quad (5b)$$

Now using the expression: $D(\lambda)=F(\lambda)*m$ for the optical density we can rewrite the equation (5b) as:

$$IR(\lambda) = I_0(\lambda)*10-2(F1(\lambda)m1 + F2(\lambda)m2 + Fp(\lambda)mp)*[R1(\lambda) + 10^{-2(F3(\lambda)m3+F4(\lambda)m4+F5(\lambda)m5}*R2(\lambda)*(1-R1(\lambda))2]*C(\Omega) \quad (6)$$

When the ophthalmic system 100 of FIG. 1 is capable of providing a significant number of wavelengths, within the visible region of the spectrum between approximately 380 nm and 720 nm, then a sufficient number of measurements are provided allowing a solution to the unknown mi values to be obtained from the multiple simultaneous equations (6). Further, from these multiple measurements estimates of the $F_i(\lambda)$ and $Ri(\lambda)$ spectral absorption, and the spectral reflection functions for each optical layer in the eye may be determined. It would be evident to one skilled in the art that using determination of oxygen saturation in retinal vessel proves to be very difficult when a limited numbers of measured wavelengths are used. However, with rapid tunable filters and fast CCDs obtaining such measurements is fast and convenient to the user.

Further, having digital data allows the process to correct for issues such as movement of the patient's retina, variations in optical source intensity etc. It would therefore be apparent to one skilled in the art that the approach provides for fast, accurate and reproducible evaluation and analysis of ocular data. Further, having time dependent wavelength data within a relatively short time period provides for correction of other factors.

Additionally, it would be apparent that upon a subsequent examination of the patient the extracted data provides for historical clinical records, which are typically not available for patient's retina, except for the rare case that the patient had images taken due to their exposure to laser sources etc.

Anomalies in wavelength dependency are optionally highlighted rapidly prior to detailed analysis, images may be optionally presented to an ophthalmic specialist as color coded variances from a previous evaluation, or a new algorithm may be employed to analyze previously stored records.

Hence, if we consider that a new technique for measuring hemoglobin is established with six wavelengths, being 535, 560, 577, 622, 636, and 670 nm, and that these are within the datasets stored for a patient then upon adding a new analysis algorithm to the ophthalmic system 100 the patient's hemoglobin data may be historically extracted. It would be evident this is advantageous in expanding clinical records on patients with evolving knowledge in the medical field, and allows subsequent analysis of clinical records to establish previously undetected conditions or determine timing of an onset of a condition or disease.

Figure 3:
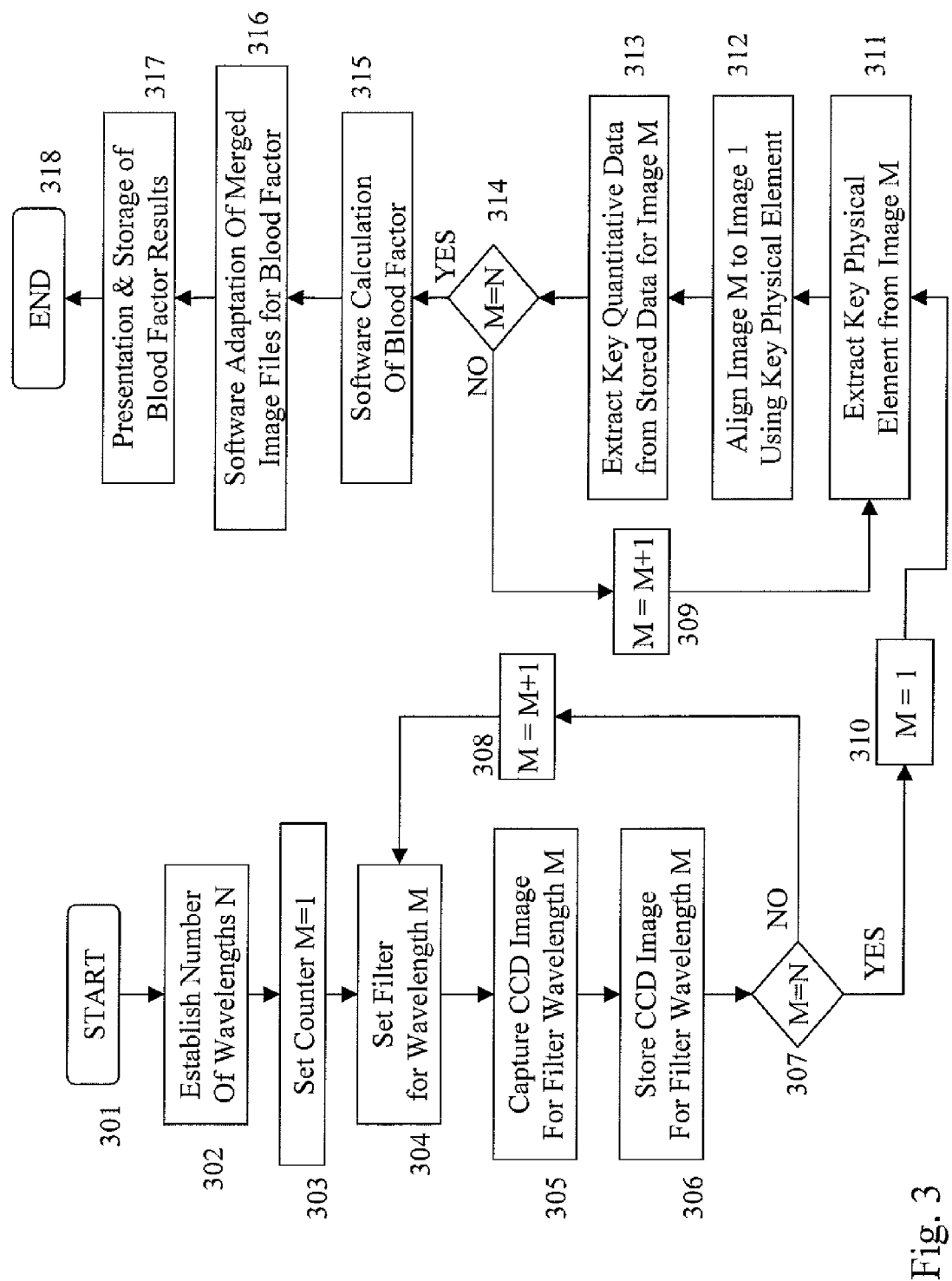
FIG. 3 illustrates an exemplary flow chart chart for providing an oximeter functionality within an exemplary embodiment of the invention for hemoglobin oxygen saturation measurements

Referring to FIG. 3 an exemplary flow diagram for an exemplary ophthalmic system 100 is shown providing an hemoximeter functionality to determine the concentration of hemoglobin (Hb), oxygenated Hb, carbon monoxide bound Hb, metallic bound Hb, and sulfurated Hb for the patient's blood using ocular image data.

As shown the process starts at step 301 with the loading of an algorithm to control the ophthalmic system. At step 302 the number of wavelengths to be measured is established from the algorithm, and at step 303 a counter M is set to 1 for the initial measurement. At step 304 a wavelength filter is set to the first wavelength, which may be a wavelength target extracted from a database in reference to the algorithm and the counter M. At step 305 the ophthalmic system captures the image of the patient's retina and in step 306, the ophthalmic system stores the extracted image.

At step 307 the algorithm establishes whether it has completed the imaging process or not. If there are additional wavelengths to be captured then the ophthalmic system returns via step 308 to step 304 in a cyclic manner until the sequence is completed. At this point, the ophthalmic system algorithm resets the counter M to 1. The algorithm then proceeds to a second analysis sequence starting at step 311 where the first wavelength image is extracted and a physical element within the image is identified.

At step 312 the algorithm aligns the extracted image to a predetermined image frame using the physical element identified. Then at step 313 key quantitative data is extracted from the image. At step 314 the algorithm establishes whether it has completed the analysis process or not. If there are additional wavelengths to be captured then the ophthalmic system returns via step 309 to step 311 in cyclic manner until the sequence is completed. In this exemplary algorithm the physical element alignment of each wavelength image allows the movement of the patient's eyeball to be removed from the images.

At step 315 a software calculation of the blood factor of interest is undertaken using the extracted quantitative data at steps 313 from the wavelength images. Next the algorithm at 316 adapts a merged image file, determined in this example by additive addition of all image files, for the blood factor. At step 317 the resulting data is formatted and presented to the patient, operator, or ophthalmic specialist as defined by the algorithm before ending at step 318. Such presentation of resulting data may be tabulated data, image data, manipulated image data, etc. An option within step 316 is to adjust the images according to the result of an analysis such that a presented image highlights a detected abnormality in results as well as the tabulated data.

It would be apparent to one skilled in the art that such digitally extracted image data can be stored not only centrally within an ophthalmic center's databases but may also be stored within a smart card embedded within a patient's health card. Such data may be beneficially extracted and analyzed for oxygen saturation in retinal arteries and retinal veins for example during a surgery in trauma and emergency environments to enhance the trauma team's knowledge of the patient's normal oxygen saturation and whether ocular measurements in trauma environments are abnormal or not. It would be further apparent that a low cost, portable variant of the ophthalmic system 100 is possible allowing its use in remote environments, within trauma rooms, within wards, etc. as well as the more conventional environments for performing routine analysis and assessment of patients.

Beneficially, the method and system presented allow for multiple ophthalmic tests and measurements to be performed from a single instrument, in a single location, without requiring the insertion/removal of multiple test elements and equipment, whilst allowing improved patient ergonomics as the system can compensate for limited eye or head movements during the tests. Further, use of relatively fast and low cost elements provides a multiple test system that optionally performs these measurements in less time than a traditional single examination test of the prior art approaches.

Numerous other embodiments may be envisaged without departing from the spirit or scope of the invention.

What is claimed is:

1. A system comprising:
   an optical source, the optical source comprising a control port, the optical source for selectably providing each of a plurality of predetermined wavelength optical signals in dependence upon a plurality of control wavelength signals, a first wavelength optical signal of the plurality of predetermined wavelength optical signals provided in response to a first control wavelength signal and other than provided in response to a second control wavelength signal, a second wavelength optical signal of the plurality of predetermined wavelength optical signals comprising light at a second wavelength absent from the first wavelength optical signal;
   a detector, the detector comprising an output port, the detector for receiving reflected optical signals, generating digital representations of the reflected optical signals, and providing the digital representations of the reflected optical signals at the output port as electrical signals;
   an optical coupling, the optical coupling for coupling the each of the plurality of predetermined wavelength optical signals to a patient's eyeball, receiving the reflected optical signals returned from the eyeball of the patient, and providing the reflected optical signals to the detector; and,
   a controller, the controller being electrically connected to the control port and the output port, the controller for providing the plurality of control wavelength signals to the control port, receiving the electrical signals from the output port, and providing processed electrical signals including a first processed electrical signal determined at least in dependence upon a first electrical signal received from the output port in response to providing the first control wavelength signal to the control port, and a predetermined factor.

2. A system according to claim 1 wherein,
   the optical source provides a second wavelength optical signal in response to the second control wavelength signal and other than in response to the first control wavelength signal; and
   the controller provides a second processed electrical signal at least in dependence upon a second electrical signal received from the output port in response to providing the second control wavelength signal to the control port, during a single sitting of the patient.

3. A system according to claim 1 wherein, the controller comprises a circuit for providing a plurality of processed electrical signals, each of the plurality of processed signals dependent upon a different predetermined characteristic of the patient's eyeball.

4. A system according to claim 1 wherein, the optical coupling comprises one of a lens, a mirror, a beam-splitter, a wavelength filter, a rest and a restraint.

5. A system according to claim 4 wherein, at least one of the rest and the restraint provide a predetermined optical configuration of at least the optical source, detector, and patient's eyeball.

6. A system according to claim 1 wherein, the optical coupling provides a predetermined optical configuration of at least the optical source, detector, and patient's eyeball.

7. A system according to claim 1 further comprising;
   a memory, the memory for storing at least the processed electrical signals.

8. A system according to claim 7 wherein, the memory comprises one of a computer memory, a computer disk drive, a computer readable storage medium, a memory drive, a memory chip, a smart card, and a networked computer disk drive.

9. A system comprising:
   an optical source, the optical source comprising a control port, for receiving a control wavelength signal, the optical source for selectably providing a first wavelength optical signal comprising light at a first wavelength and a second wavelength optical signal comprising light at a second wavelength, the selection between the first wavelength and the second wavelength dependent upon the control wavelength signal, the first wavelength different than the second wavelength;
   a detector comprising an output port, the detector
      for receiving a first reflected optical signal and for providing a first digital representation of the first reflected optical signal at the output port as a first electrical signal, and
      for receiving a second reflected optical signal and for providing a second digital representation of the second reflected optical signal at the output port as a second electrical signal;
   an optical coupling, the optical coupling for
      coupling the first wavelength optical signal to a patient's eyeball, receiving the first reflected optical signal returned from the eyeball of the patient, and providing the first reflected optical signal to the detector,
      coupling the second wavelength optical signal to a patient's eyeball, receiving the second reflected optical signal returned from the eyeball of the patient, and providing the second reflected optical signal to the detector; and
   a controller, the controller being electrically connected to the control port and the output port, the controller for providing the control wavelength signal to the control port, receiving the first electrical signal and second electrical signal from the output port, and providing a first processed electrical signal and a second processed electrical signal, the first processed electrical signal being determined at least in dependence upon the first electrical signal, the first control wavelength signal, and a first predetermined factor, and the second processed electrical signal being determined at least in dependence upon the second electrical signal, the second control wavelength signal, and a second predetermined factor.

10. A system according to claim 9 wherein,
coupling the first wavelength optical signal comprises coupling the first wavelength optical signal to the patient's first eyeball;
coupling the second wavelength optical signal comprises coupling the second wavelength optical signal to the patient's first eyeball; and
coupling the first wavelength optical signal to the patient's first eyeball and coupling the second wavelength optical signal to the patient's first eyeball occurs in sequence and during a single sitting of the patient.

11. A system according to claim 9 wherein the first electrical signal is provided at $t_1$ and the second electrical signal is provided at $t_2$, $t_1$ different than $t_2$.

12. A system according to claim 9 wherein the first predetermined factor and the second predetermined factor are in dependence upon a characteristic of the patient's eyeball.

13. A system according to claim 9 wherein the controller comprises a circuit for providing the first processed electrical signal and the second processed electrical signal, the first processed electrical signal and the second processed electrical signal obtained without a reconfiguration of the system and comprising a reconfiguration circuit that is other than operated during a single sitting of the patient.

14. A system according to claim 9 wherein, the controller comprises a circuit for providing the first processed electrical signal and for providing the second processed electrical signal, the first processed electrical signal and the second processed electrical signal dependent upon a different predetermined characteristic of the patient's eyeball.

15. A system according to claim 9 wherein, the optical source further comprises a tunable laser for being tuned to the first wavelength optical signal and the second wavelength optical signal in dependence upon different control wavelength signals provided to the control port.

16. A system according to claim 1 wherein, the optical source further comprises a tunable optical filter for being tuned to pass one of the first wavelength and the second wavelength in dependence upon different control wavelength signals provided to the control port.

17. A system according to claim 1 wherein, the optical source comprises a first predetermined optical filter and a second predetermined optical filter, one of the first predetermined optical filter and the second predetermined optical filter selected in dependence upon different control wavelength signals provided to the control port.

18. A system according to claim 1 wherein, the optical source comprises a first light source and a second light source, one of the first light source and the second light source selected in dependence upon different control wavelength signals provided to the control port.

19. A system according to claim 2 wherein, the controller comprises a circuit for providing the plurality of processed electrical signals, each of the plurality of processed signals obtained without a reconfiguration of the system other than providing at least a subset of the plurality of optical wavelengths and comprising a reconfiguration circuit that is other than operated during the patient sitting.

20. A system according to claim 3 comprising, a sequencer for providing the optical wavelength signals comprising known wavelengths of light in a predetermined sequenced fashion in accordance with predetermined characteristics of the patient's eyeball.

21. A system according to claim 1 wherein, the controller comprises a circuit for providing the plurality of processed electrical signals, each of the plurality of processed signals dependent upon a different sensed characteristic of the patient's eyeball.

22. A system according to claim 3 comprising a sequencer for providing the optical wavelength signals comprising known wavelengths of light in a sequenced fashion in accordance with the sensed characteristics of the patient's eyeball.

23. A system according to claim 1 wherein the controller comprises a circuit for providing the plurality of processed electrical signals, each of the plurality of processed electrical signals obtained without a reconfiguration of the system other than providing at least a subset of the plurality of optical wavelengths.

24. A system according to claim 1 wherein the optical source further comprises a tunable laser for being tuned to different wavelengths in dependence upon different control wavelength signals provided to the control port.

25. A system according to claim 1 wherein the optical source further comprises a tunable optical filter for being tuned to pass different wavelengths in dependence upon different control wavelength signals provided to the control port.

26. A system according to claim 1 wherein the optical source comprises a plurality of predetermined optical filters, each one of the plurality of optical filters selected in dependence upon different control wavelength signals provided to the control port.

27. A system according to claim 1 wherein the optical source comprises a plurality of light sources, each one of a plurality of light sources selected in dependence upon different control wavelength signals provided to the control port.

28. A system according to claim 27 wherein the light sources comprise solid state light emitting diodes.

* * * * *